US012791106B2

(12) United States Patent
Mason et al.

(10) Patent No.: US 12,791,106 B2
(45) Date of Patent: Nov. 10, 2026

(54) UMBRELLA CHECK VALVE

(71) Applicant: CareFusion 303, Inc., San Diego, CA (US)

(72) Inventors: Eugene Mason, La Habra Heights, CA (US); George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/800,484

(22) Filed: Aug. 12, 2024

(65) Prior Publication Data

US 2024/0401710 A1 Dec. 5, 2024

Related U.S. Application Data

(63) Continuation of application No. 18/302,388, filed on Apr. 18, 2023, now Pat. No. 12,098,774, which is a
(Continued)

(51) Int. Cl.
*F16K 15/02* (2006.01)
*A61M 5/14* (2006.01)
(Continued)

(52) U.S. Cl.
CPC ......... *F16K 15/023* (2013.01); *A61M 5/1414* (2013.01); *A61M 39/24* (2013.01);
(Continued)

(58) Field of Classification Search
CPC ............................. F16K 15/023; F16K 15/148
See application file for complete search history.

(56) References Cited

U.S. PATENT DOCUMENTS 2,128,050 A 8/1938 Landis
2,462,189 A 2/1949 Hess
(Continued)

FOREIGN PATENT DOCUMENTS

CN 1799965 A 7/2006
CN 1946959 A 4/2007
(Continued)

OTHER PUBLICATIONS

Canadian Office Action for Application No. 3,074,832, Feb. 28, 2025, 6 pages.

(Continued)

*Primary Examiner* — Nicole Gardner
(74) *Attorney, Agent, or Firm* — MASCHOFF BRENNAN

(57) ABSTRACT

A check valve includes a housing that includes an inlet port, an outlet port, and a valve chamber. The inlet port extends from a ceiling of the valve chamber to an outer surface of the housing. The outlet port extends from a floor of the valve chamber to the outer surface of the housing. The check valve further includes a valve member supported within the chamber. The valve includes a valve head. When an upstream pressure is applied to the valve, the valve head is configured to deflect away from the ceiling of the valve chamber and unseal the inlet port. When a downstream pressure is applied to the valve, the valve head is configured to deflect away from the floor of the valve chamber and seal the inlet port such that the valve head conforms to a shape of the ceiling of the valve chamber.

20 Claims, 4 Drawing Sheets

Related U.S. Application Data continuation of application No. 16/125,469, filed on Sep. 7, 2018, now Pat. No. 11,662,033.

(60) Provisional application No. 62/557,100, filed on Sep. 11, 2017.

(51) Int. Cl.
*A61M 39/24* (2006.01)
*F16K 15/06* (2006.01)

(52) U.S. Cl.
CPC ..... *F16K 15/06* (2013.01); *A61M 2039/2466* (2013.01); *A61M 2039/2473* (2013.01)

(56) References Cited

U.S. PATENT DOCUMENTS

| | | | |
|---|---|---|---|
| 3,889,710 | A | 6/1975 | Brost |
| 4,513,784 | A | 4/1985 | Farrand |
| 4,762,149 | A | 8/1988 | Pickl, Jr. |
| 4,946,448 | A | 8/1990 | Richmond |
| 5,176,658 | A | 1/1993 | Ranford |
| 5,218,993 | A | 6/1993 | Steinberg |
| 6,409,707 | B1 | 6/2002 | Guala |
| 6,889,707 | B2 | 5/2005 | Nicolino |
| 7,438,090 | B2 | 10/2008 | Steele |
| 10,544,757 | B2 | 1/2020 | Fujisaki |
| 10,704,700 | B2 | 7/2020 | Harashima |
| 2011/0308650 | A1 | 12/2011 | Amirouche et al. |
| 2019/0024810 | A1 | 1/2019 | Harashima |

FOREIGN PATENT DOCUMENTS

| | | | |
|---|---|---|---|
| CN | 101077433 | A | 11/2007 |
| CN | 102872487 | A | 1/2013 |
| DE | 4309262 | A1 | 6/1994 |
| EP | 1093828 | A2 | 4/2001 |
| JP | H03077871 | U | 8/1991 |
| JP | H07507381 | A | 8/1995 |
| JP | 2007010124 | A | 1/2007 |
| JP | 2016056902 | A | 4/2016 |
| WO | WO-2005123175 | A1 | 12/2005 |

OTHER PUBLICATIONS

Australian Office Action for Application No. 2018327342, dated Jun. 6, 2023, 4 pages.
Australian Office Action for Application No. 2024200185, dated Sep. 18, 2024, 3 pages.
Chinese Notification to Grant for Application No. 202210539451.7, dated May 31, 2024, 4 pages including translation.
Chinese Office Action for Application No. 201880058676.2, dated Aug. 25, 2021, 19 pages including translation.
Chinese Office Action for Application No. 202210539451.7, dated Dec. 26, 2023, 15 pages including translation.
European Office Action for Application No. 21179772.5, dated Jun. 20, 2024, 9 pages.
Extended European Search Report for Application No. 21179772.5, dated Sep. 24, 2021, 7 pages.
International Preliminary Report on Patentability for Application No. PCT/US2018/049987, dated Dec. 13, 2019, 21 pages.
International Search Report and Written Opinion for Application No. PCT/US2018/049987, dated Dec. 6, 2018, 13 pages.
Japanese Office Action for Application No. 2020-514510, dated Aug. 9, 2022, 7 pages including translation.
Japanese Office Action for Application No. 2023-061804, dated May 2, 2024, 5 pages including translation.
Written Opinion of the International Preliminary Examining Authority for Application No. PCT/US2018/049987, dated Aug. 16, 2019, 8 pages.
European Office Action for Application No. 21179772.5, dated Mar. 10, 2026, 7 pages.
Canadian Office Action for Application No. 3,074,832, Jan. 30, 2026, 4 pages.
Japanese Office Action for Application No. 2024-188858, dated Dec. 3, 2025, 6 pages including translation.
Japanese Office Action for Application No. 2024-188858, dated Jun. 9, 2026, 11 pages including translation.

UMBRELLA CHECK VALVE

CROSS-REFERENCE TO RELATED APPLICATIONS

This application is a continuation of U.S. patent application Ser. No. 18/302,388, entitled "Umbrella Check Valve," filed Apr. 18, 2023, which is a continuation of U.S. patent application Ser. No. 16/125,469, entitled "Umbrella Check Valve," filed Sep. 7, 2018, now U.S. Pat. No. 11,662,023, which claims priority under 35 U.S.C. § 119 to U.S. Provisional Application No. 62/557,100, entitled "Umbrella Check Valve," filed on Sep. 11, 2017, the disclosures of which are incorporated herein by reference in their entireties.

TECHNICAL FIELD

The present disclosure generally relates to the administration of medication by infusion and, more particularly, to a check valve.

BACKGROUND

A bag, bottle, syringe, or other container that contains infusion medication or solution is hung from a rack to administer the infusion solution. A tube is connected between the container and an infusion pumping system. A catheter at the end of the tube is inserted into a patient for an intravenous (IV) infusion. The tube may be part of an assembly that includes fittings, connectors, check valves, and pumping elements and is frequently referred to as an "IV set." The infusion solution is administered to the patient when the infusion pumping system is started.

Existing IV check valves include chambers that include inlet ports disposed on the upstream of the IV check valves and outlet ports disposed on the downstream of the IV check valves. The inlet ports allow the fluid to flow from the tube into the check valves, and the outlet ports allow the fluid to flow out of the check valves into the tube.

SUMMARY

IV check valves are normally closed when there is no movement of fluid (e.g., infusion solution) through the IV set. For example, when there is no movement of fluid, the check valve is closed and does not allow fluid to pass the inlet port. When the fluid flows through the IV set, IV check valves open and allow the fluid to flow from one end of the IV check valve to the other end. However, many valves are susceptible to lodging grit and particulates. When reverse flow is applied while the grit is lodged, the inlet port does not fully seal and creates a small leak which renders the valve to be useless.

Providing an IV check valve that prevents grit lodging that leads to leaks and backflows of the fluid would be advantageous. Providing an infusion pump that accomplishes this while also being more reliable, less expensive, and/or quieter than current infusion pumps would be an additional advantage. Described herein are check valves that achieve these desired functions and objectives.

A check valve includes a housing that includes an inlet port, an outlet port, and a valve chamber. The inlet port extends from a ceiling of the valve chamber to an outer surface of the housing. The outlet port extends from a floor of the valve chamber to the outer surface of the housing. The check valve further includes a valve member supported within the chamber. The valve includes a valve head. When an upstream pressure is applied to the valve, the valve head is configured to deflect away from the ceiling of the valve chamber and unseal the inlet port. When a downstream pressure is applied to the valve, the valve head is configured to deflect away from the floor of the valve chamber and seal the inlet port such that the valve head conforms to a shape of the ceiling of the valve chamber.

A check valve system includes an inlet housing that has an inlet port and an outlet housing that has an outlet port. The check valve system further includes a valve chamber created by engaging the inlet housing and the outlet housing. An inner surface of the inlet housing serves as a ceiling of the valve chamber. An inner surface of the outlet housing serves as a floor of the valve chamber. The check valve system also includes an umbrella-shaped valve supported within the valve chamber. When an upstream pressure is applied to the umbrella-shaped valve, the umbrella-shaped valve is configured to move away from the inlet port and create a gap between the ceiling of the valve chamber and an upper surface of the umbrella-shaped valve. When a downstream pressure is applied to the umbrella-shaped valve, the umbrella-shaped valve is configured to deflect away from the outlet port, and the upper surface of the umbrella-shaped valve conforms to a shape of the ceiling of the valve chamber.

A check valve includes a valve chamber comprising an inlet port at an inlet end, an outlet port at an outlet end, a ceiling, and a floor. The inlet port extends from the ceiling to outside of the valve chamber, and the outlet port extends from the floor to outside of the valve chamber. The check valve also includes a valve supported within the valve chamber. The curved floor includes a dome shape and is raised at a center of the curved floor. A periphery of the curved floor is closer to the outlet end than the center of the curved floor.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The disclosed embodiments of IV check valves provide a reliable method of delivering a fluid preventing backflow of the fluid.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The methods and systems disclosed herein are presented in terms of an infusion pump for the delivery of medical fluid to a patient. It will be apparent to those of ordinary skill in the art that the disclosed concepts may be applied to a variety of mechanisms utilizing check valves.

Figure 1:
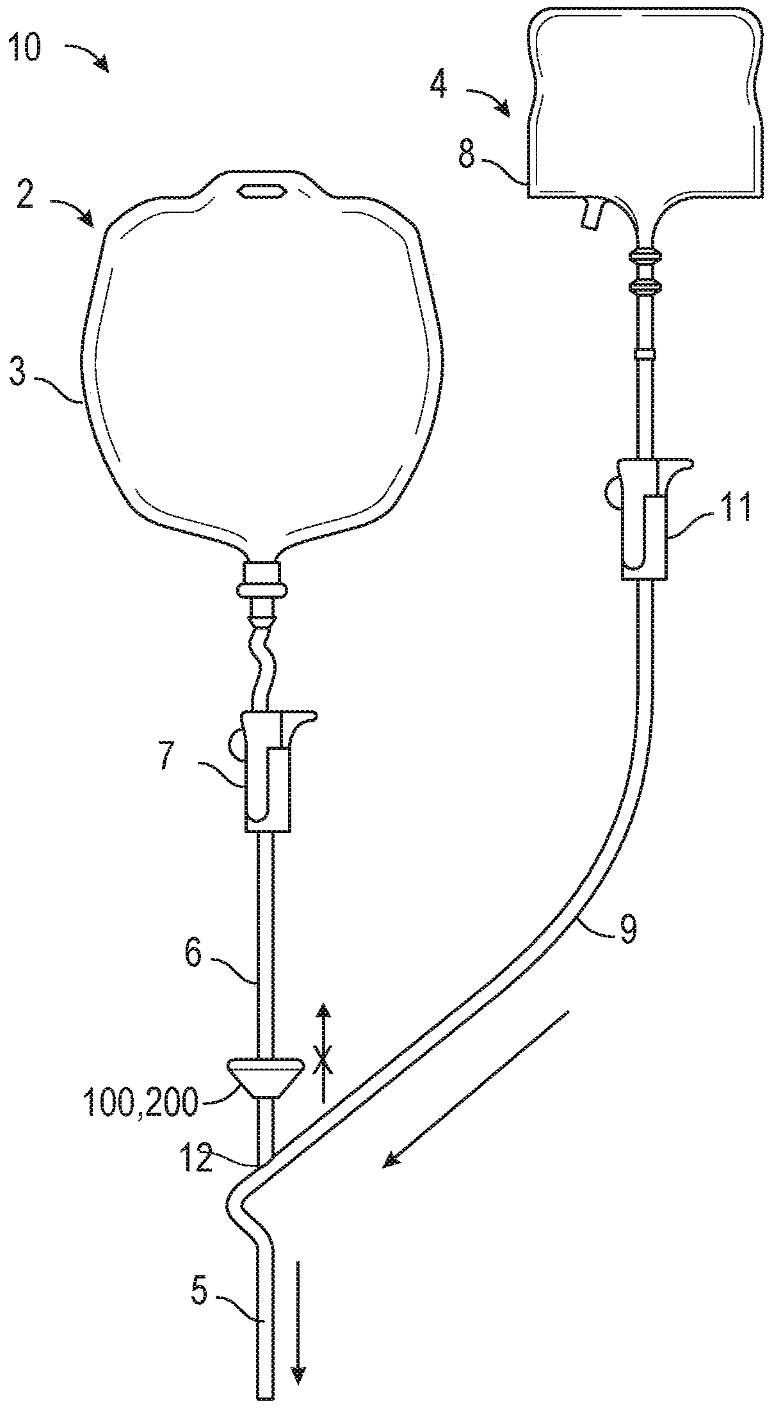
FIG. 1 depicts a perspective view of an IV set having a check valve according to certain aspects of the disclosure.

FIG. 1 depicts a perspective view of an IV set 10 having a check valve 100, 200 according to certain aspects of the disclosure. As illustrated in FIG. 1, an IV set 10 includes an IV check valve 100, 200 therein. IV set 10 includes a main fluid system 2 and an auxiliary fluid system 4. An IV pump (not shown) receives fluid from main fluid system 2 and branch or auxiliary fluid system 4 via a supply line 5 and controls and dispenses the fluids therefrom to a patient.

Main fluid system 2 includes a main fluid source such as a fluid bag 3 which may include or contain saline solution or other fluid to be administered to the patient. As illustrated, tube 6 carries flow from a drip chamber 7 to a Y-connector 12. Check valve 100, 200 is disposed in tube 6 upstream from the Y-connector 12 and enables flow from fluid bag 3 to the IV pump (not illustrated) while preventing reverse flow (backflow) of fluid from auxiliary fluid system 4 toward fluid bag 3.

Auxiliary fluid system 4 includes an auxiliary fluid source such as a fluid bag 8 which may contain drugs or other fluid to be supplied to the patient for treatment. An auxiliary fluid line 9 carries flow from drip chamber 11 to the Y-connector 12.

Aspects of the subject technology relate to a check valve 100, 200 that prevents backflow of fluid (e.g., infusion medication or saline solution).

Figure 2:
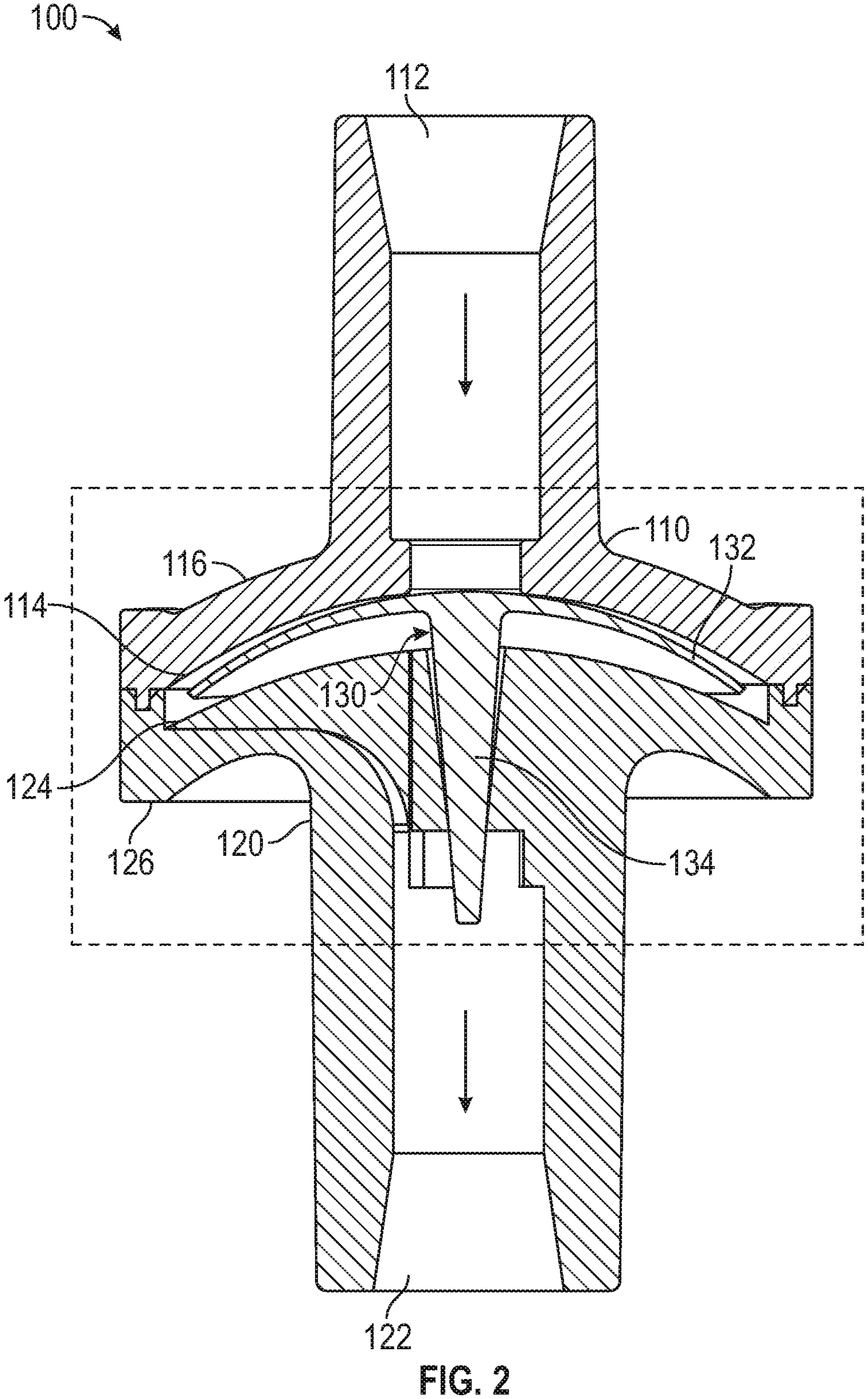
FIG. 2 depicts a cross-sectional view of an IV check valve according to certain aspects of the disclosure.

FIG. 2 illustrates a check valve 100 that includes an inlet housing 110, an outlet housing 120, and a valve 130. The inlet housing 110 includes an inlet port 112, a first inner surface 114, and a first outer surface 116. The inlet port 112 extends from the first inner surface 114 to the first outer surface 116 of the inlet housing 110. The outlet housing 120 includes an outlet port 122, a second inner surface 124, and a second outer surface 126. The outlet port 122 extends from the second inner surface 124 to the second outer surface 126 of the outlet housing 120. The valve 130 includes a valve head 132 and a stem 134.

Figure 3:
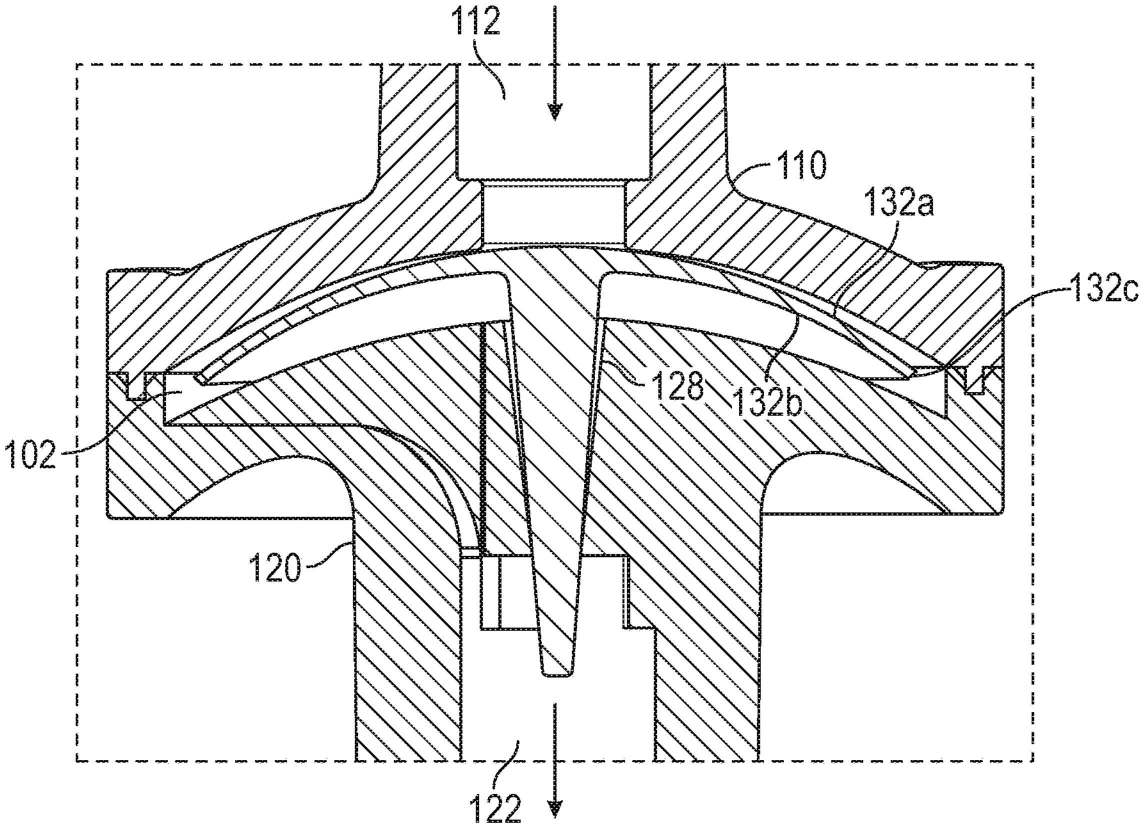
FIG. 3 depicts an enlarged partial cross-sectional view of the IV check valve of FIG. 2 according to certain aspects of the disclosure.

FIG. 3 illustrates an enlarged partial cross-sectional view of a valve portion of the check valve 100. The inlet housing 110 and the outlet housing 120 engage and create a valve chamber 102. The valve 130 is disposed within the valve chamber 102. The valve head 132 of the valve 130 includes an upper surface **132*a*, a lower surface 132*b*, and a periphery 132*c*. The stem 134 extends downwardly, which can be generally perpendicularly, from the lower surface 132*b* and is retained in an aperture or hole 128 of the outlet housing 120**.

The inlet port 112 of the inlet housing 110 may connected to a tube 6 of an IV set (illustrated in FIG. 1) and allow the fluid to flow from the tube 6 into the check valve 100. When there is no movement of the fluid, the central portion of the upper surface **132*a* of the valve head 132 is configured or predisposed to abut against the rim of the opening of the inlet port 112 in the chamber 102 and seals the inlet port 112. The area of the central portion sealing the inlet port 112 may be slightly larger than the area of the stem 134 that is in contact with the lower surface 132*b* of the valve head 132. As illustrated in FIG. 2, there is a gap between the periphery 132*c* of the valve head 132 and the first inner surface of the inlet housing 110. The gap becomes gradually smaller as it gets closer to the central portion of the upper surface 132*a* from the periphery 132*c***.

When the fluid moves in the direction of the arrows shown in FIGS. 2 and 3, an upstream pressure (a pressure directed from the upstream direction to the downstream direction) is applied to the valve head 132. The upstream pressure presses the valve head 132 towards the stem 134 and deflects the valve head 132 away from the opening of the inlet port 112 to create a gap between the first inner surface 114 of the inlet housing 110 and the upper surface **132*a* of the valve head 132. The fluid flows through the gap and over the upper surface 132*a* of the valve 132 towards the periphery 132*c*. The fluid flows into the outlet port 122 of the outlet housing 120** and into and along the tube of the IV set.

When the movement of fluid slows down and a downstream pressure (a pressure directed from the downstream direction to the upstream direction) is applied to the valve head 132, the central portion of the upper surface **132*a* and other portions of the valve head 132, including the periphery 132*c*, contacts the inner surface 114 of the inlet housing 110. For example, when the downstream pressure is applied, the valve head 132 deflects away from the outlet housing 120, and closes the gap between the upper surface 132*a* of the valve head 132 and the first inner surface 114 of the inlet housing 110. The radius of the valve head 132 is greater than the diameter of grit or a particulate that may lodge between the first inner surface 114 and the upper surface 132*a*. With this structure, even in the case when grit or particulates lodge between the first inner surface 114 and the upper surface 132*a*, the rest of the upper surface 132*a* is in contact with the first inner surface 114 so that the opening of the inlet port 112 in the valve chamber 102** is securely sealed.

In some aspects, the valve chamber 102 may have a dome-shaped ceiling (e.g., first inner surface 114) as shown in FIGS. 2 and 3. The curvature of the dome-shaped ceiling may be less than the curvature of the upper surface **132*a* of the valve head 132 when there is no movement of fluid. The difference in the degree of curvature of the dome-shaped ceiling and that of the upper surface 132*a* allows the center of the upper surface 132*a* of the valve head 132 to be in contact with the rim of the opening of the inlet port 112 in the valve chamber while the periphery 132*c* of the valve head 132 and the dome-shaped ceiling do not engage with each other. The curvature of the dome-shaped ceiling and the curvature of the upper surface 132*a* of the valve head 132 may facilitate grit and particulates to flow downstream preventing lodging of grit and particulates between the first inner surface 114 and the upper surface 132***a*. In some aspects, the valve chamber 102 may have a curved floor (e.g., second inner surface 124) where the floor is raised as it moves towards the center of the floor as shown in FIGS. 2 and 3. Further, in some other aspects, the grit and particulates that have passed the passage between the first inner surface 114 and the upper surface 132*a* may be collected on the floor of the valve chamber 102 near the second inner surface 124.

In some aspects, the material of the valve 130 may be silicone or elastomeric material. The thickness of the valve head 132 decreases from the center to the periphery 132*c* as illustrated in FIGS. 2 and 3. This structure facilitates the periphery 132*c* to easily move towards the first inner surface 114 when the downstream pressure is applied.

Figure 4:
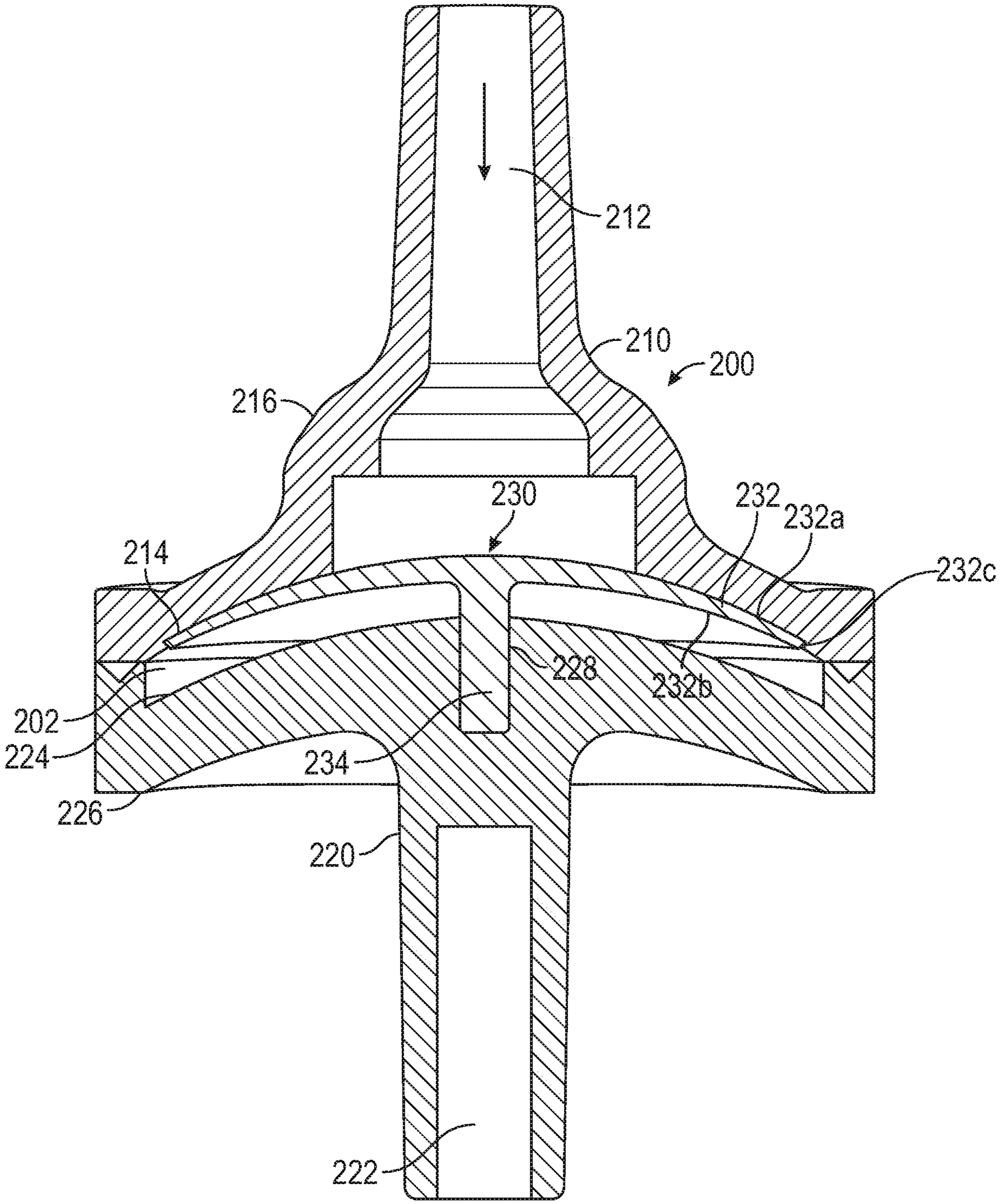
FIG. 4 depicts a cross-sectional view of an IV check valve according to certain aspects of the disclosure.

FIG. 4 depicts a cross-sectional view of an IV check valve 200 according to certain aspects of the disclosure. As illustrated in FIG. 4, the check valve 200 is in the closed state, where the check valve 200 restricts fluid flow in the reverse direction, i.e., backflow (from the outlet port 222 to the inlet port 212), in accordance with some embodiments of the present disclosure. As depicted, the check valve 200 includes an inlet housing 210, an outlet housing 220, and a valve 230. The inlet housing 210 includes an inlet port 212, a first inner surface 214, and a first outer surface 216. The inlet port 212 extends from the first inner surface 214 to the first outer surface 216 of the inlet housing 210. The outlet housing 220 includes an outlet port 222, a second inner surface 224, and a second outer surface 226. As depicted, the outlet port 222 extends from the second inner surface 224 to the second outer surface 226 of the outlet housing 220. Similar to the valve 130 of FIGS. 2 and 3, the valve 230 includes a valve head 232 and a stem 234.

In some embodiments, the inlet housing 210 engages and is coupled to the outlet housing 220 to define a valve chamber 202. The valve 230 is disposed within the valve chamber 202. The valve head 232 of the valve 230 includes an upper surface 232*a*, a lower surface 232*b*, and a periphery 232*c*.

The stem 234 extends downwardly, which can be generally perpendicularly, from the lower surface 232*b* and is retained in an aperture or hole 228 of the outlet housing 220.

The inlet port 212 of the inlet housing 210 may be connected to a tube 6 of an IV set (illustrated in FIG. 1) and allow the fluid to flow from the tube 6 into the check valve 200. The check valve 200 differs in structure from the check valve 100 in that a diameter of the opening of the inlet port 212 which is fluidly communicated with the valve chamber 202 is greater than that of the opening of the inlet port 112. Thus, when there is no movement of the fluid, a greater area of the upper surface 232*a* nominally engages the inner surface 214 of the inlet housing 210 to seal the inlet port 212, as compared to the embodiments of FIGS. 2 and 3 where only the central portion of the upper surface 132*a* of the valve head 132 is configured to abut against the rim of the opening of the inlet port 112. As depicted in FIG. 4, since a greater surface area of the upper surface 232*a* is exposed to the fluid flowing through the inlet port 212, a reduced amount of force is required to displace the valve 230 in the downstream direction and unseal the inlet port 212. Advantageously, due to the increased surface area of the valve 230 that is exposed to the fluid flow, cracking (opening) pressure of the valve 230 is reduced as compared to the embodiments of FIGS. 2 and 3.

As depicted in FIG. 4, the area of the upper surface 232*a* sealing the inlet port 212 is substantially larger than the area of the stem 234 that is in contact with the lower surface 232*b* of the valve head 232. When the fluid moves in the direction of the arrows shown in FIG. 4, an upstream pressure is applied to the valve head 232. The upstream pressure presses the valve head 232 towards the stem 234 and deflects the valve head 232 away from the opening of the inlet port 212 to create a gap between the first inner surface 214 of the inlet housing 210 and the upper surface 232*a* of the valve head 232. The fluid flows through the gap, over the upper surface 232*a* of the valve 232 towards the periphery 232*c*, into the outlet port 222 of the outlet housing 220 and into and along the tube 6 of the IV set (illustrated in FIG. 1).

When the movement of fluid slows down and a downstream pressure is applied to the valve head 232, the area of the upper surface 232*a* directly below the inlet port 212, and other portions of the valve head 232, including the periphery 232*c*, contact the inner surface 214 of the inlet housing 210. For example, when the downstream pressure is applied, the valve head 232 deflects away from the outlet housing 220, and closes the gap between the upper surface 232*a* of the valve head 232 and the first inner surface 214 of the inlet housing 210. Similar to the embodiments of FIGS. 2 and 3, the radius of the valve head 232 is greater than the diameter of grit or a particulate that may lodge between the first inner surface 214 and the upper surface 232*a*. With this structure, even in the case when grit or particulates lodge between the first inner surface 214 and the upper surface 232*a*, the rest of the upper surface 232*a* is in contact with the first inner surface 214 so that the opening of the inlet port 212 in the valve chamber 202 is securely sealed.

Similar to the embodiments of FIGS. 2 and 3, the valve chamber 202 may have a dome-shaped ceiling (e.g., first inner surface 214) as shown in FIG. 4. The curvature of the dome-shaped ceiling may be less than the curvature of the upper surface 232*a* of the valve head 232 when there is no movement of fluid. In contrast to the embodiments of FIGS. 2 and 3, in the closed position, as illustrated in FIG. 4, the periphery 232*c* of the valve head 232 and the dome-shaped ceiling engage with each other to seal the inlet port 212. Thus, when an upstream pressure is applied to the upper surface 232*a* of the valve 230, the entire valve 230 is displaced in the downstream direction thereby unsealing the inlet port 212. The configuration of the various embodiments of FIG. 4 is advantageous in that it is not necessary for the entire valve to compress down on the stem 234 in order to open the valve 230.

As illustrated in FIG. 4 the curvature of the dome-shaped ceiling and the curvature of the upper surface 232*a* of the valve head 232 may facilitate grit and particulates to flow downstream preventing lodging of grit and particulates between the first inner surface 214 and the upper surface 232*a*. In some aspects, the valve chamber 202 may have a curved floor (e.g., second inner surface 224) where the floor is raised as it moves towards the center of the floor as shown in FIG. 4. Further, in some other aspects, the grit and particulates that have passed the passage between the first inner surface 214 and the upper surface 232*a* may be collected on the floor of the valve chamber 202 near the second inner surface 224.

In some aspects, the material of the valve 230 may be silicone or elastomeric material. As illustrated in FIG. 4, the thickness of the valve head 232 decreases from the center to the periphery 232*c*. This structure facilitates the periphery 232*c* to easily move towards the first inner surface 214 when the downstream pressure is applied.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An IV check valve, comprising:

an inlet housing, an outlet housing, and a valve chamber formed between an inner surface of the inlet housing and an inner surface of the outlet housing, the inlet housing comprising an inlet port forming a first fluid passage extending from a first opening through the inner surface of the inlet housing to an outer surface of the inlet housing, and the outlet housing comprising an outlet port forming a second fluid passage extending from a second opening through the inner surface of the outlet housing to an outer surface of the outlet housing; and a valve member comprising a valve head and a valve stem, the valve member positioned within the valve chamber with a central portion of an upper surface of the valve head engaged against the first opening, a gap between a periphery of the upper surface of the valve member and the inner surface of the inlet housing, and the valve stem extending longitudinally from the valve head to the outlet housing;

wherein when a pressure from the inlet housing is applied to the valve member, the valve head is bendable away from the inner surface of the inlet housing to an open position in which the upper surface of the valve head unseals from the first opening, and when a pressure from the outlet housing is applied to the valve member, the valve head is bendable toward the inner surface of the inlet housing to a closed position in which the upper surface of the valve head seals the first opening such that the valve head conforms to a shape of the inner surface of the inlet housing and the gap between the periphery of the upper surface of the valve member and the inner surface of the inlet housing is closed.

2. The IV check valve of claim 1, wherein the first opening defines an area of the inner surface of the inlet housing engaged against the upper surface of the valve head, and the second opening defines an area of the inner surface of the outlet housing engaged against the valve stem, the area of the second opening being smaller than the area of the first opening.

3. The IV check valve of claim 1, wherein the valve member comprises an umbrella-like shape.

4. The IV check valve of claim 1, wherein the inner surface of the inlet housing comprises a dome shape.

5. The IV check valve of claim 1, wherein the upper surface of the valve head is configured to engage against a rim of the first opening.

6. The IV check valve of claim 1, wherein a thickness of the valve head decreases from the central portion towards a periphery of the valve head.

7. The IV check valve of claim 1, wherein the valve stem is positioned within the second opening.

8. The IV check valve of claim 1, wherein the valve stem extends into and is retained in the second opening.

9. The IV check valve of claim 8, wherein, when the pressure from the outlet housing is applied to the valve member, the valve head is bendable in a direction away from the valve stem.

10. An IV check valve, comprising:

an inlet housing, an outlet housing, and a valve chamber formed between an inner surface of the inlet housing and an inner surface of the outlet housing, the inlet housing comprising an inlet port forming a first fluid passage extending from a first opening through the inner surface of the inlet housing to an outer surface of the inlet housing, and the outlet housing comprising an outlet port forming a second fluid passage extending from a second opening through the inner surface of the outlet housing to an outer surface of the outlet housing; and a valve member comprising a valve head and a valve stem, the valve member positioned within the valve chamber with a central portion of an upper surface of the valve head engaged against the first opening, a gap between a periphery of the upper surface of the valve member and the inner surface of the inlet housing, and the valve stem extending longitudinally from the valve head to the outlet housing;

wherein, in an open position, the valve head is biased in a direction away from the inner surface of the inlet housing such that the upper surface of the valve head unseals from the first opening, and in a closed position, the valve head is biased in a direction toward the inner surface of the inlet housing such that the upper surface of the valve head seals the first opening, the valve head conforms to a shape of the inner surface of the inlet housing, and the gap between the periphery of the upper surface of the valve member and the inner surface of the inlet housing is closed.

11. The IV check valve of claim 10, wherein the first opening defines an area of the inner surface of the inlet housing engaged against the upper surface of the valve head, and the second opening defines an area of the inner surface of the outlet housing engaged against the valve stem, the area of the second opening being smaller than the area of the first opening.

12. The IV check valve of claim 10, wherein the valve member comprises an umbrella-like shape.

13. The IV check valve of claim 10, wherein the inner surface of the inlet housing comprises a dome shape.

14. The IV check valve of claim 10, wherein the upper surface of the valve head is configured to engage against a rim of the first opening.

15. The IV check valve of claim 10, wherein a thickness of the valve head decreases from the central portion towards a periphery of the valve head.

16. The IV check valve of claim 10, wherein the valve stem is positioned within the second opening.

17. A method for providing an IV check valve, the method comprising:

providing an inlet housing and an outlet housing such that a valve chamber is formed between an inner surface of the inlet housing and an inner surface of the outlet housing, the inner surface of the inlet housing comprising a first opening and a first fluid passage extending from the first opening to an outer surface of the inlet housing, and the inner surface of the outlet housing comprising a second opening and a second fluid passage extending from the second opening to an outer surface of the outlet housing; and providing a valve member comprising a valve head and a valve stem, the valve member positioned within the valve chamber with a central portion of an upper surface of the valve head engaged against the first opening, a gap between a periphery of the upper surface of the valve member and the inner surface of the inlet housing, and the valve stem extending longitudinally from the valve head to the outlet housing;

wherein in an open position, the valve head is biased in a direction away from the inner surface of the inlet housing such that the upper surface of the valve head unseals from the first opening, and in a closed position, the valve head is biased in a direction toward the inner surface of the inlet housing such that the upper surface of the valve head seals the first opening and the valve head conforms to a shape of the inner surface of the inlet housing to close the gap between the periphery of the upper surface of the valve member and the inner surface of the inlet housing.

18. The method of claim 17, wherein providing the valve member comprises the upper surface of the valve head engaged against a rim of the first opening.

19. The method of claim 17, wherein providing the valve member comprises the valve stem positioned within the second opening.

20. The method of claim 17, wherein the valve stem extends into and is retained in the second opening such that, when the valve head moves toward the closed position, the valve head is configured to bias in a direction away from the valve stem.

* * * * *